(12) United States Patent
Yamazaki et al.

(10) Patent No.: US 6,453,203 B1
(45) Date of Patent: Sep. 17, 2002

(54) ELECTRODE TIGHTS FOR PULSE SHAPE-UP APPARATUS

(75) Inventors: Iwao Yamazaki; Yoshihiro Izawa, both of Tokyo (JP)

(73) Assignee: Ya - Man Ltd., Tokyo (JP)

( * ) Notice: Subject to any disclaimer, the term of this patent is extended or adjusted under 35 U.S.C. 154(b) by 0 days.

(21) Appl. No.: 09/509,526

(22) PCT Filed: Oct. 5, 1998

(86) PCT No.: PCT/JP98/04492
§ 371 (c)(1),
(2), (4) Date: Mar. 31, 2000

(87) PCT Pub. No.: WO99/17835
PCT Pub. Date: Apr. 15, 1999

(30) Foreign Application Priority Data

Oct. 3, 1997 (JP) .............................................. 9-288009
Oct. 8, 1997 (JP) .............................................. 9-291706

(51) Int. Cl.[7] .................................................. A61N 1/00
(52) U.S. Cl. ...................................... 607/149; 607/152
(58) Field of Search ........................... 604/20; 607/115, 607/149, 152

(56) References Cited

U.S. PATENT DOCUMENTS 2,667,162 A * 1/1954 Zwahlen
6,151,528 A * 11/2000 Maida

* cited by examiner

*Primary Examiner*—Mark Bockelman
(74) *Attorney, Agent, or Firm*—Jones, Tullar & Cooper, P.C.

(57) ABSTRACT

A pair of electrode tights which does not require that one be naked when lying down to take a beauty treatment. Six pairs of flat electrodes EL1 to EL6, ER1 to ER6 are attached to selected places symmetrical relative to the center fine inside of the garment, with the flat electrodes facing the underbelly, the inguinal region, the hip, the femoral region, the rear side of the knee and the calf of the body. These flat electrodes are connected to a pulse beauty treatment apparatus via electrically conductive press studs and a bundle of electric wires. The pair of electrode tights may have an elongated tubular bag for containing the bundle of electric wires. The elongated tubular bag has a fastener running along its full length for holding together two parts of the bag, and a plurality of relay terminals fixed inside for connecting the electric wires to the flat electrodes.

1 Claim, 13 Drawing Sheets

ELECTRODE TIGHTS FOR PULSE SHAPE-UP APPARATUS

TECHNICAL FIELD

The present invention relates to a pulse beauty treatment apparatus whose electric pulse supply applies a train of electric pulse voltage to selected portions of the body with the aid of electrodes, thereby electrically stimulating the body for beauty treatment, and more particularly to electrodes used in such a pulse beauty treatment apparatus.

BACKGROUND ART

Bioelectric current is flowing ceaselessly in the body to assist cells with their activities and muscles with their constriction.

The pulse beauty treatment apparatus can supply a train of pulse current to the body for stimulation, thereby activating cells even more and muscular contraction for improving the function of the body as the bioelectric current would do in flowing in the body.

In the pulse beauty treatment apparatus sucking electrodes are applied to selected portions of the body as in electro-cardiography. Alternatively clamp electrodes are used, pinching selected portions of the body.

Such electrodes, however, cannot be applied to selected portions of the body with ease, and their application areas are so limited that they are not sure to cover selected areas of the body without fail. A flat narrow or band-like electrode or a large four-sided or sheet-like electrode is large in area, and can be applied to a selected portion of the body with ease. These electrodes have aluminum foils applied to the narrow or four-sided pieces of rubber or cloth. A band-like electrode is wound round a selected portion of the body. A sheet-like electrode is laid on the mat, and one lies down on the sheet-like electrode with his back or front upside.

The sheet-like electrode, however, restrains one from assuming one's postures other than laying oneself down on the sheet-like electrode, and therefore, one is fatigable in one's fixed posture. The winding of the band-like electrode round the selected portion of the body is apt to restrain one's activity. Inconveniently one cannot take such a beauty treatment without taking one's wear off.

SUMMARY OF THE INVENTION

The object of the present invention is to provide an electrode structure which permits one to take any desired posture while taking a beauty treatment, totally free of any restriction such as in the conventional sheet-like electrode requiring that one be naked to lie on the sheet-like electrode.

The invention has a pair of electroded tights for use in a pulse beauty treatment apparatus, which pair of electroded tights made of stretch material has flat electrodes of flexible, soft material fixed to selected portions of the inner surface of the garment, the flat electrodes being adapted to be connected to an associated pulse generator. The invention further has a pair of electroded tights for use in a pulse beauty treatment apparatus, which pair of electroded tights has a bundle of electric wires connected to its flat electrodes, the bundle of electric wires being contained in an elongated tubular bag, which has opening-and-closing means for opening the elongated tubular bag wide along its full length, and a plurality of relay terminals attached inside for making electric connections between the flat electrodes and the electric wires.

DESCRIPTION OF THE PREFERRED EMBODIMENTS

A pair of electrode tights according to one preferred embodiment of the present invention is described below.

Figure 1:
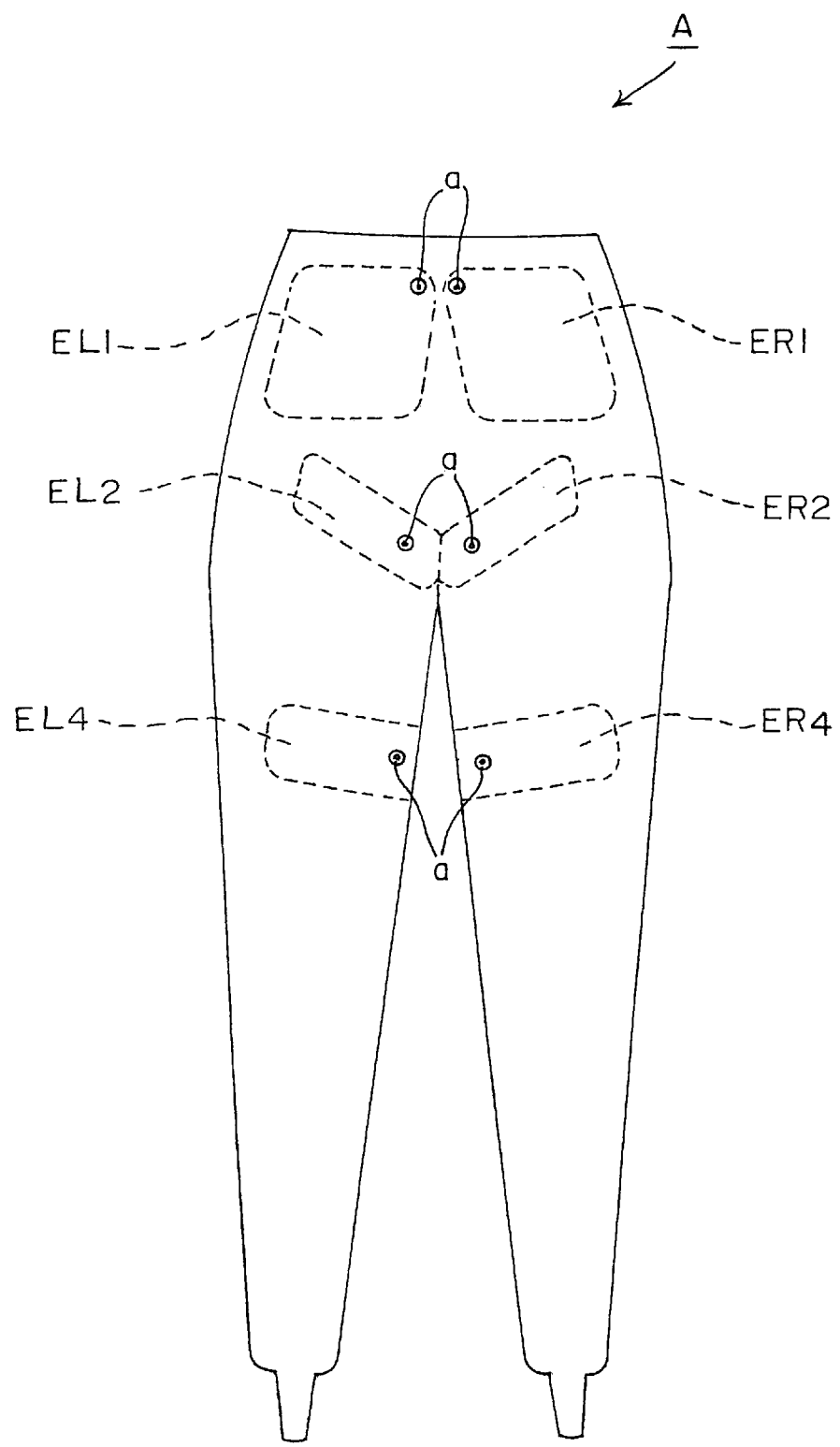
FIG. 1 is a front view of a pair of electroded tights.
Figure 2:
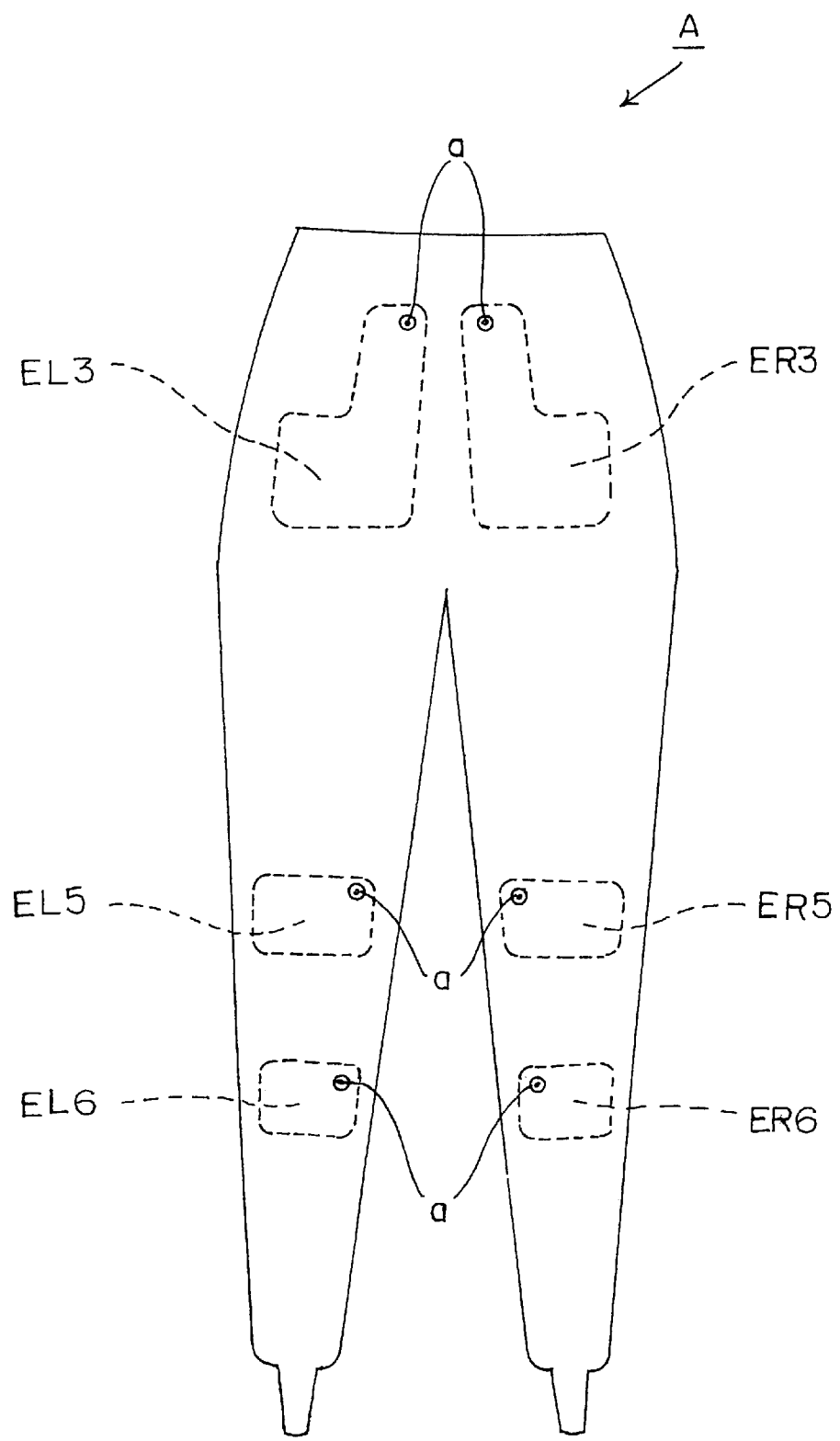
FIG. 2 is a rear view of the pair of electroded tights.

Referring to FIGS. 1 and 2 the pair of electrode tights A has six pairs of flat electrodes EL1 and ER1; EL2 and ER2; EL3 and ER3; EL4 and ER4; EL5 and ER5; and EL6 and ER6 applied inside. These electrodes will be applied to the lower part of the body, particularly to the underbelly, the inguinal region, the hip, the femoral region, the rear side of the knee and the calf of the body when the pair of electrode tights A is worn on the body.

The pair of tights is made of expandable fabric to provide a very close fitting garment covering the legs and lower part of the body with its flat electrodes applied to the selected portions of the body.

The pair of tights has twelve electrically conductive press studs "a".

Figure 3:
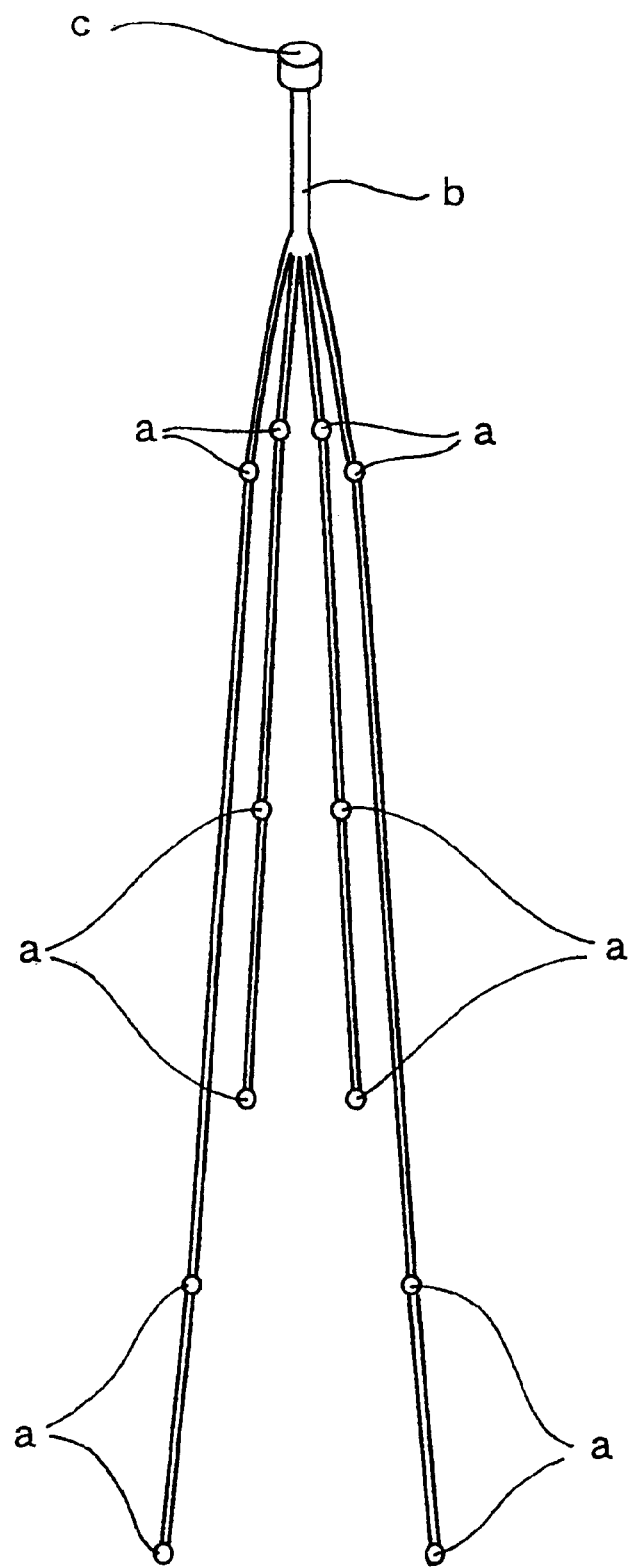
FIG. 3 is a plane view of a bundle of electric wires.

FIG. 3 shows twelve electric wires of different lengths, which are used in connecting the flat electrodes EL1 to EL6 and ER1 to ER6 to the pulse beauty treatment apparatus. These electric wires are divided in four series-connections each of three electric wires, and the four series-connections are gathered at their one ends as indicated by "b", ending with an electric connector C, by means of which the electric wires can be connected to the pulse beauty treatment apparatus.

The twelve electrically conductive press studs "a" permit detachable connection of the flat electrodes EL1 to EL6 and ER1 to ER6 to the pulse beauty treatment apparatus.

The flat electrodes are sheets of urethane coated with carbon ink.

These flat electrodes are sewed on selected areas of the garment with their coatings facing inward; the selected areas will be put on the underbelly, the inguinal region, the hip, the femoral region, the rear side of the knee and the calf of the body when the pair of electroded tights A is worn on the body.

Figure 4:
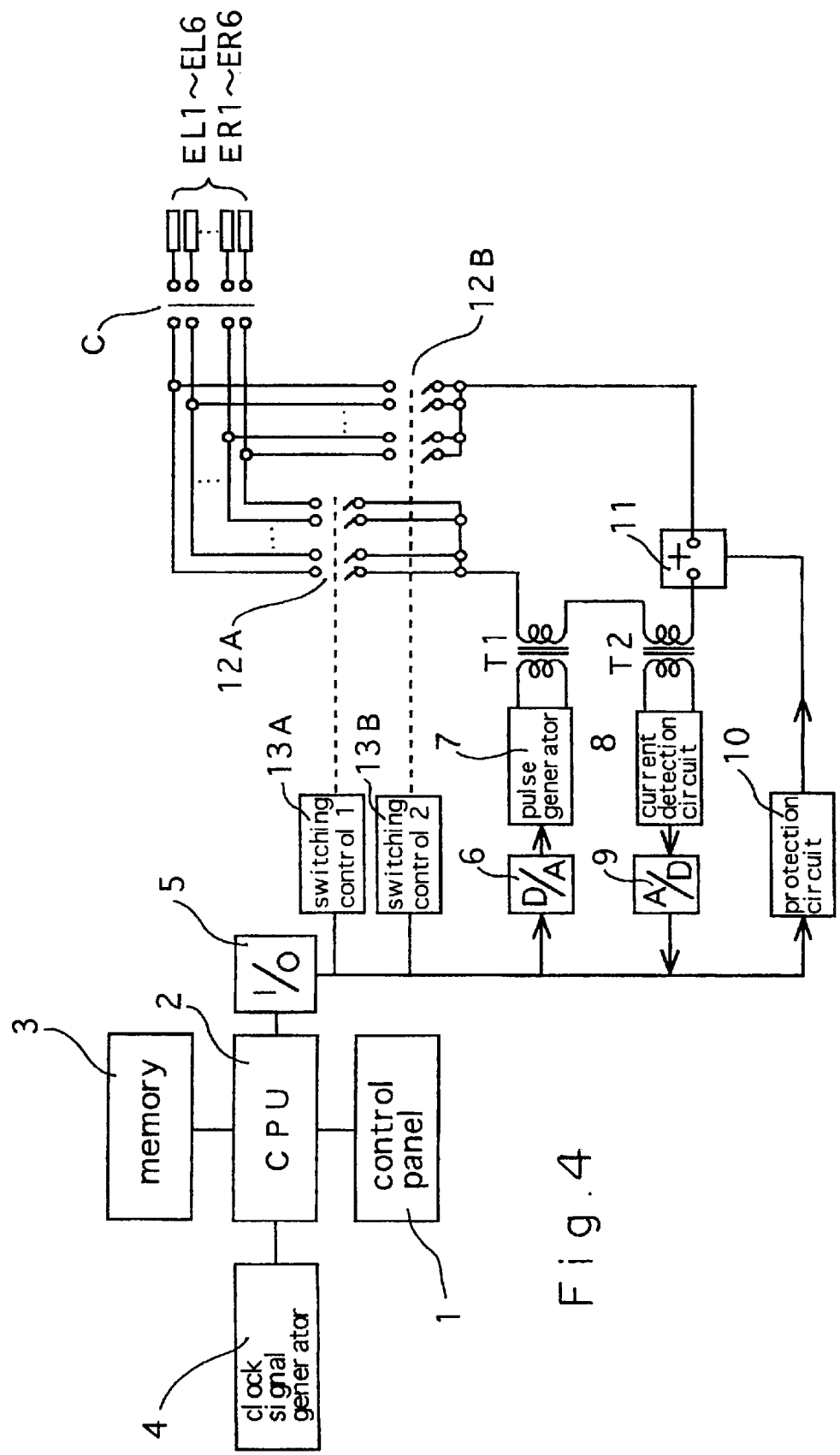
FIG. 4 is a block diagram of a pulse beauty treatment 30 apparatus.

FIG. 4 shows a pulse beauty treatment apparatus. It comprises a console 1, a CPU 2, a memory 3, a clock signal generator 4, an interface 5, a digital-to-analog converter 6, a pulse generator 7, a current detector 8, an analog-to-digital converter 9, a protection circuit 10, a breaker 11, and switching circuits 12A and 12B. A desired kind of beauty treatment and a desired pulse-application pattern are selectively read from the memory 3 with the aid of the CPU 2, and the reference clock signal generator 4 is so controlled that the clock pulses may be divided to provide digital trigger signals to meet the demand. The trigger signals are directed to the pulse generator 7 via the interface 5 and the D/A converter 6, thus permitting the pulse generator 7 to produce pulses of predetermined width and recurrence, which are directed to the primary winding of an associated transformer T1. The current detector 8 is connected to another transformer T2 parallel-connected to the transformer T1, thereby watching and making a decision as to whether or not an excessive current is flowing.

The electric current thus detected is directed to the CPU 2 via the A/D converter 9 and the I/D interface 5, so that the CPU2 may permit the protection circuit 10 to respond to the rise of the electric current beyond the threshold value for actuating the breaker 11.

The switching circuits 12A and 12B are connected to the series-connection of the secondary windings of the transformers T1 and T2. The flat electrodes EL1 to EL6 an ER1 to ER6 are connected to the switching circuits 12A and 12B via the connector C.

The switching circuits 12A and 12B are so designed as to perform their switching actions via associated photocouplers, which are responsive to signals from associated selectors 13A and 13B for making electric connections between the pulse generator and selected flat electrodes.

Thus, the flat electrodes EL1 to EL6 and ER1 to ER6 are selectively combined to allow pulse currents to flow in the so selected flat electrodes in such a pulse-application pattern that the desired beauty treatment may be effected on the body.

More specifically, one contact is selected among the contacts each of the switching circuits 12A and 12B, and the two contacts thus selected are closed to provide two closed circuits including two flat electrodes associated with the selected and closed contacts and the selected portions of the body facing the two flat electrodes. Thus, the selected portions of the body are stimulated by pulses from the pulse generator 7 for beauty treatment.

One kind of beauty treatment is called "toning", which can be carried out by applying pulses at a relatively low recurrence ranging from 5 to 10 Hz, thereby giving stimulation to a deep point in the body to cause the skeletal muscle movement, thereby expediting the blood circulation and kneading the selected portion of the body. Another kind of beauty treatment is called "drainage", which can be carried out by applying pulses at a relatively high recurrence ranging from 20 to 100 Hz, thereby giving stimulation to a shallow point in the body to cause the muscle movement under the skin, thereby expediting the flow of lymph in the body and reducing dropsies, if any.

Special "toning" or "drainage" uses up-and-down cyclic variation of pulse voltage, thereby giving cyclic variable stimulation to the body.

In the ordinary "toning" or "drainage" pulse current is allowed to flow in all of the electrodes simultaneously. In the time-sequential "toning" or time-sequential "drainage" pulse current is allowed to flow in groups of electrodes one after another, and in the time-divisional "toning" or time-divisional "drainage", pulse current is allowed to flow in some selected groups of electrodes simultaneously.

Basic modes of pulse-application in a pair of electroded tights include a symmetrical pulse-application pattern; an alternate pulse-application pattern; and a mother-and-daughter pulse-application pattern.

Figure 5:
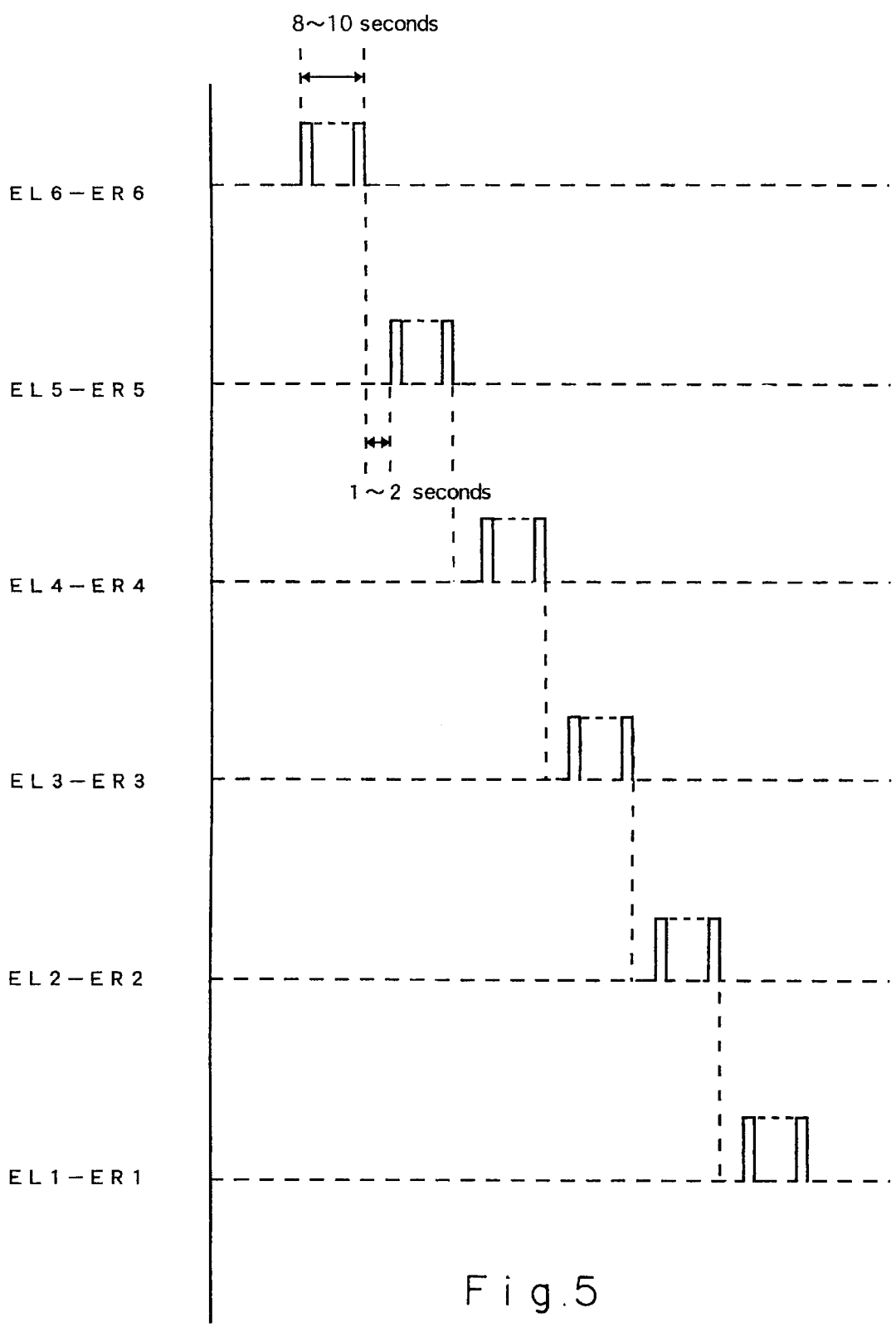
FIG. 5 is a time-varying diagram showing a symmetrical pulse-application pattern for pulsing stimulation.

Referring to FIG. 5, symmetrically paired, left and right flat electrodes EL6 and ER6; EL5 and ER5; EL4 and ER4; EL3 and ER3; EL2 and ER2; and finally EL1 and ER1 are supplied with electric pulse sequentially in the symmetrical pulse-application pattern, thus stimulating the calf, the rear side of the knee, the femoral region, the hip, the inguinal region and the underbelly of the body in the order named. Paired flat electrodes are supplied with pulses for the period of eight to ten seconds, and one to two second-long break appears before application of pulses to the subsequent paired electrodes.

Figure 6:
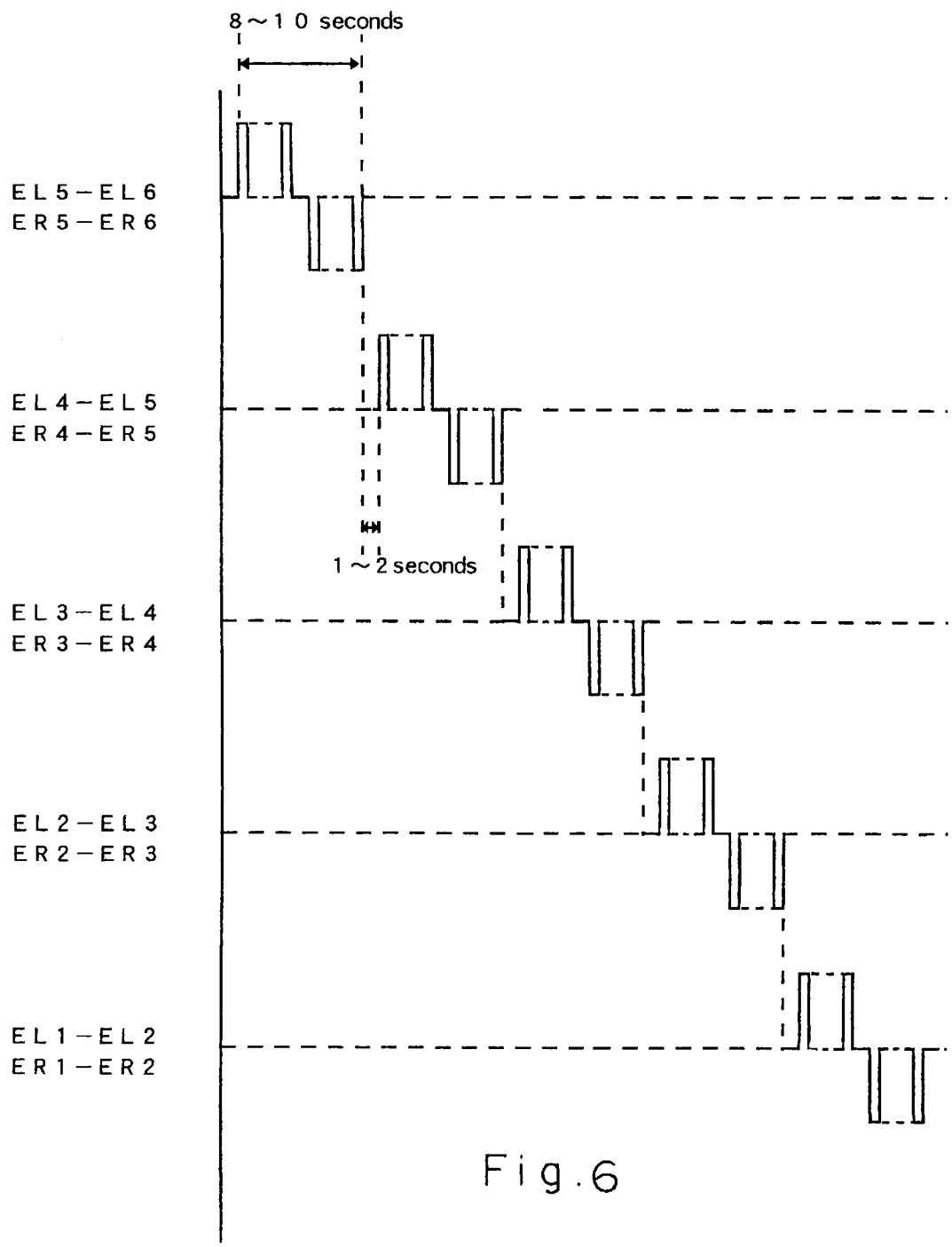
FIG. 6 is a time-varying diagram showing a corresponding pulse-application pattern for pulsing stimulation.

Referring to FIG. 6, two adjacent flat electrodes EL5-EL6, ER5-ER6; EL4-EL5, ER4-ER5; EL3-EL4, ER3-ER4; EL2-EL3, ER2-ER3; and EL1-EL2, ER1-ER2 are supplied with electric pulse in the corresponding pulse-application pattern, thus stimulating, on either side, the rear side of the knee and the calf, the femoral region and the rear side of the knee; the hip and the femoral region; the inguinal region and the hip; and the underbelly and the inguinal region. Thus, the portions of the body supplied with pulses are selected sequentially to come closer to the center of the body. Positive and negative pulses are applied to selected paired portions of the body for the period of eight to ten seconds, and one to two second-long break appears before application of positive and negative pulses to subsequent paired electrodes.

Figure 7:
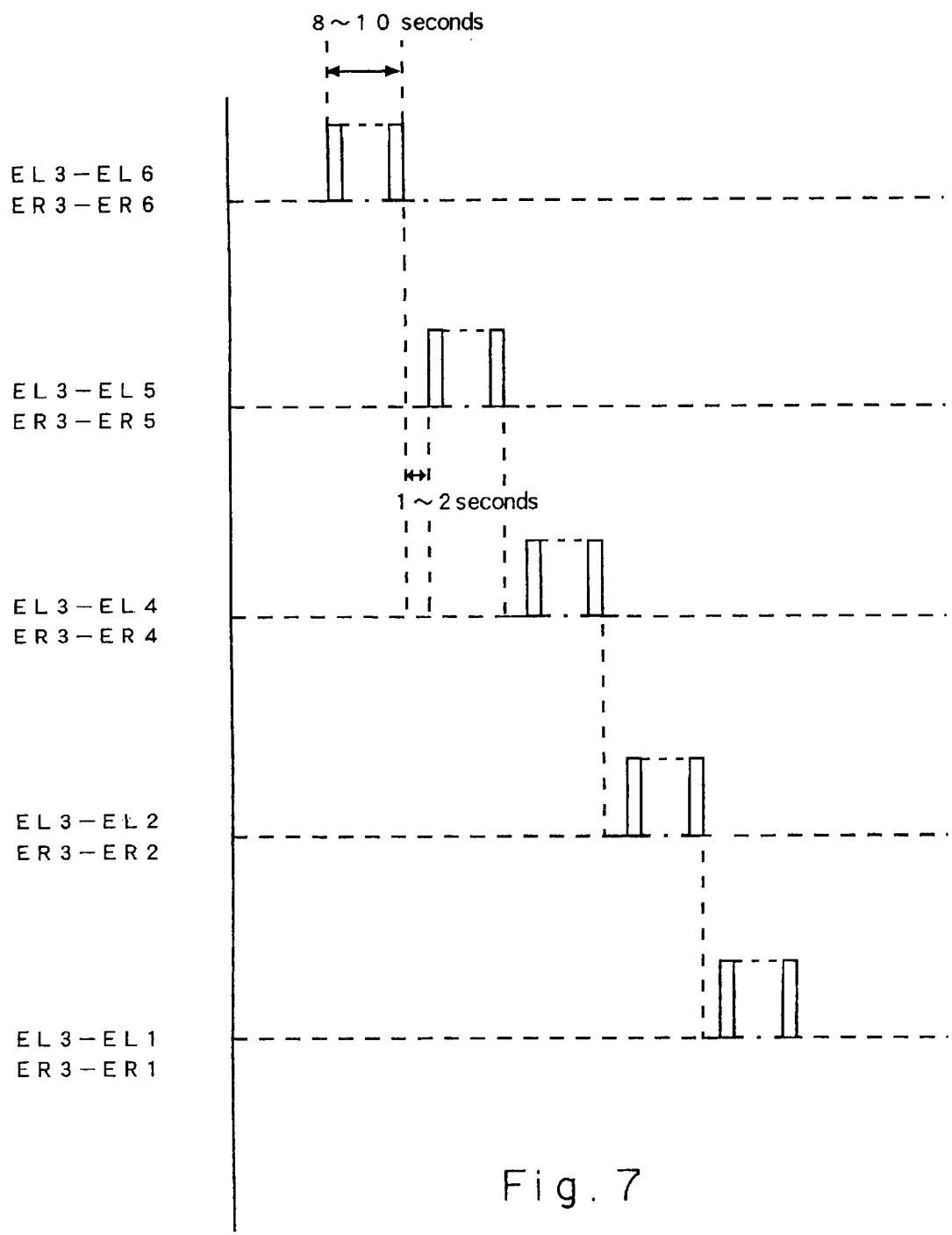
FIG. 7 is a time-varying diagram showing a mother-and-daughter pulse application pattern for pulsing stimulation.

Referring to FIG. 7, the flat electrodes EL3 and ER3 facing the hip of the body are selected as mother electrodes, and one and the other mother electrode are combined with one and counter daughter electrodes selected among those electrodes other than the mother electrodes. One set of two mother-and-daughter electrode combinations EL3-EL6 and ER3-ER6 are supplied with electric pulse simultaneously, and then another set of two mother-and-daughter electrode combinations EL3-EL5 and ER3-ER5 are supplied with electric pulse simultaneously, and so forth in the mother-and-daughter pulse-application pattern, thus stimulating the calf, the rear side of the knee, the femoral region, the inguinal region and the underbelly of the body in the order named while stimulating the hip all the time. Thus, the portions of the body supplied with pulses are selected sequentially to come closer to the center of the body. Pulses are applied to each of the mother-and-daughter combinations for the period of eight to ten seconds, leaving one to two second-long break before application of pulses to subsequent mother-and-daughter electrode combination.

In these pulse-application patterns pulsating stimulation is displaced toward the center of the body to stimulate muscles at different portions of the body, thereby driving the lymph and blood toward the heart. As a result the lymph is not allowed to be stagnant, and the circulation of blood is expedited.

The tight fitting and covering of the legs and lower part of the body in cooperation with the pulsating stimulation has the effect of preventing appearance of dropsy, which otherwise, would appear on the leg while standing and working an elongated time.

Figure 8:
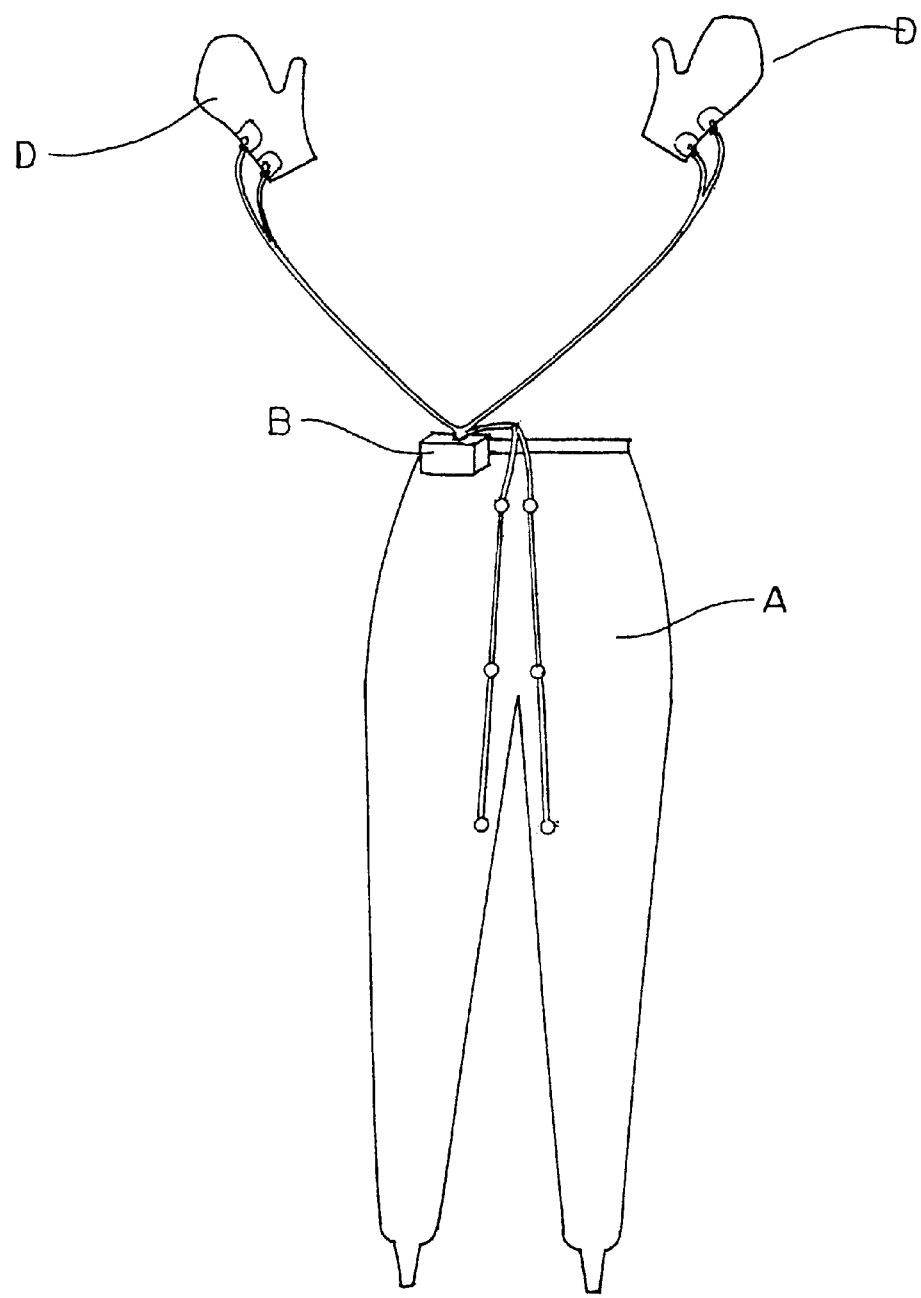
FIG. 8 illustrates a pair of electroded tights as being connected to a pair of gloves and a portable pulse beauty treatment apparatus.

Referring to FIG. 8, a pair of electroded tights A can be connected to a portable beauty treatment apparatus B, thus conveniently allowing a wearer to work or walk freely while taking a beauty treatment.

Also, the pair of electroded tights A can be connected to a pair of electroded gloves D to improve the treatment effect.

Now, the manner in which a pair of electroded tights according to the present invention is used is described below.

Figure 9:
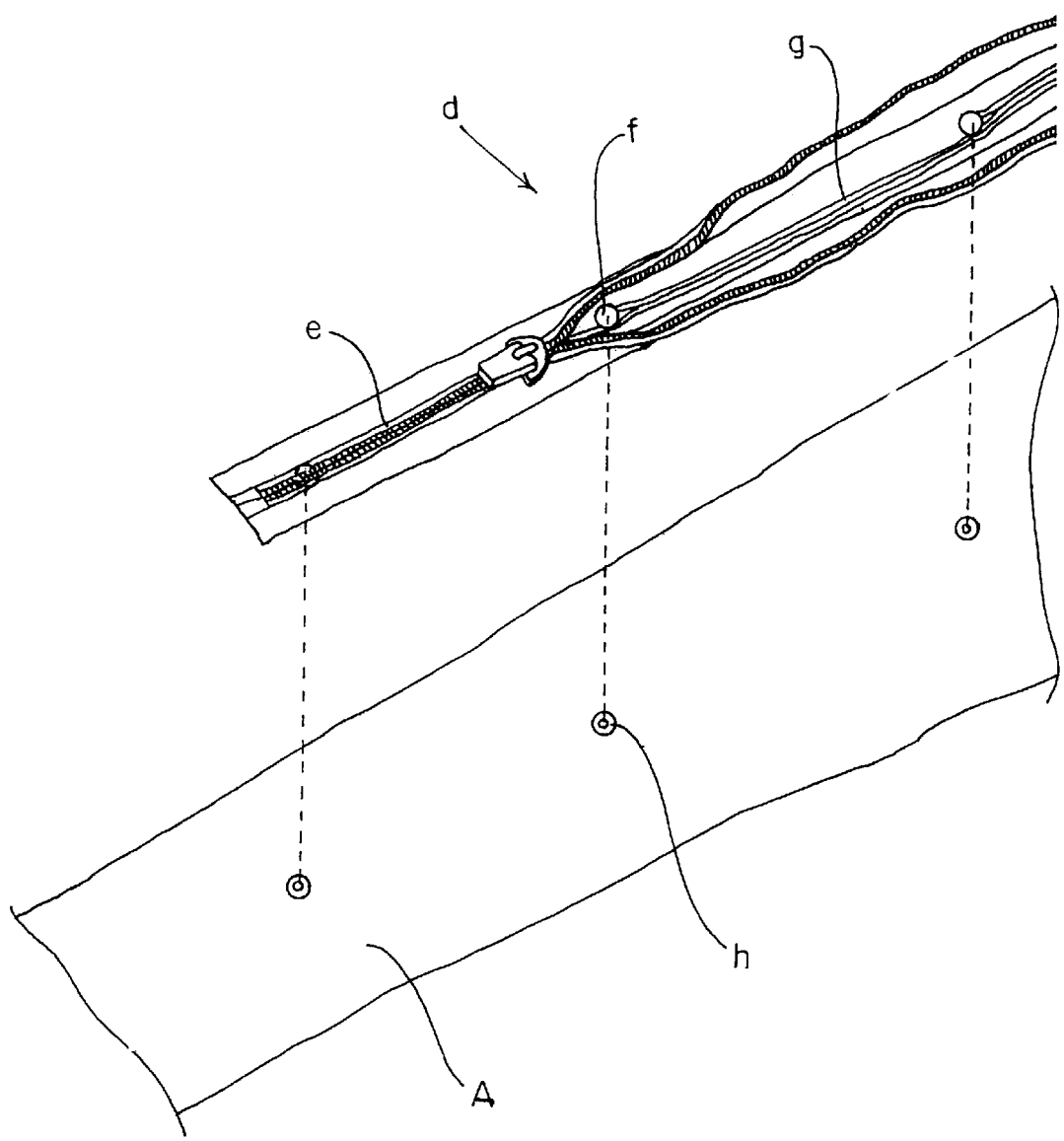
FIG. 9 illustrates an elongated tubular bag partly unfastened to show inside.

FIG. 9 illustrates an elongated tubular bag for containing a bundle of electric wires.

The elongated tubular bag "d" is made of a cloth, and it has a fastener "e" attached to its full length for holding together two parts of the tubular bag "d", and a plurality of relay terminals "f" fixed inside. The relay terminals "f" pass through the thickness of the cloth to be exposed inside and outside. Electric wires "g" are connected to the relay terminals "f" inside, and the relay terminals "f" snap in the electrically conductive press studs "h" of the pair of electroded tights outside.

The elongated tubular bag "d" is unfastened to open wide. A bundle of electric wires "g" are put in the elongated tubular bag, and their ends are connected to the relay terminals "f". Then, the tubular bag "d" is closed to contain the bundle of the electric wires inside.

Figure 10:
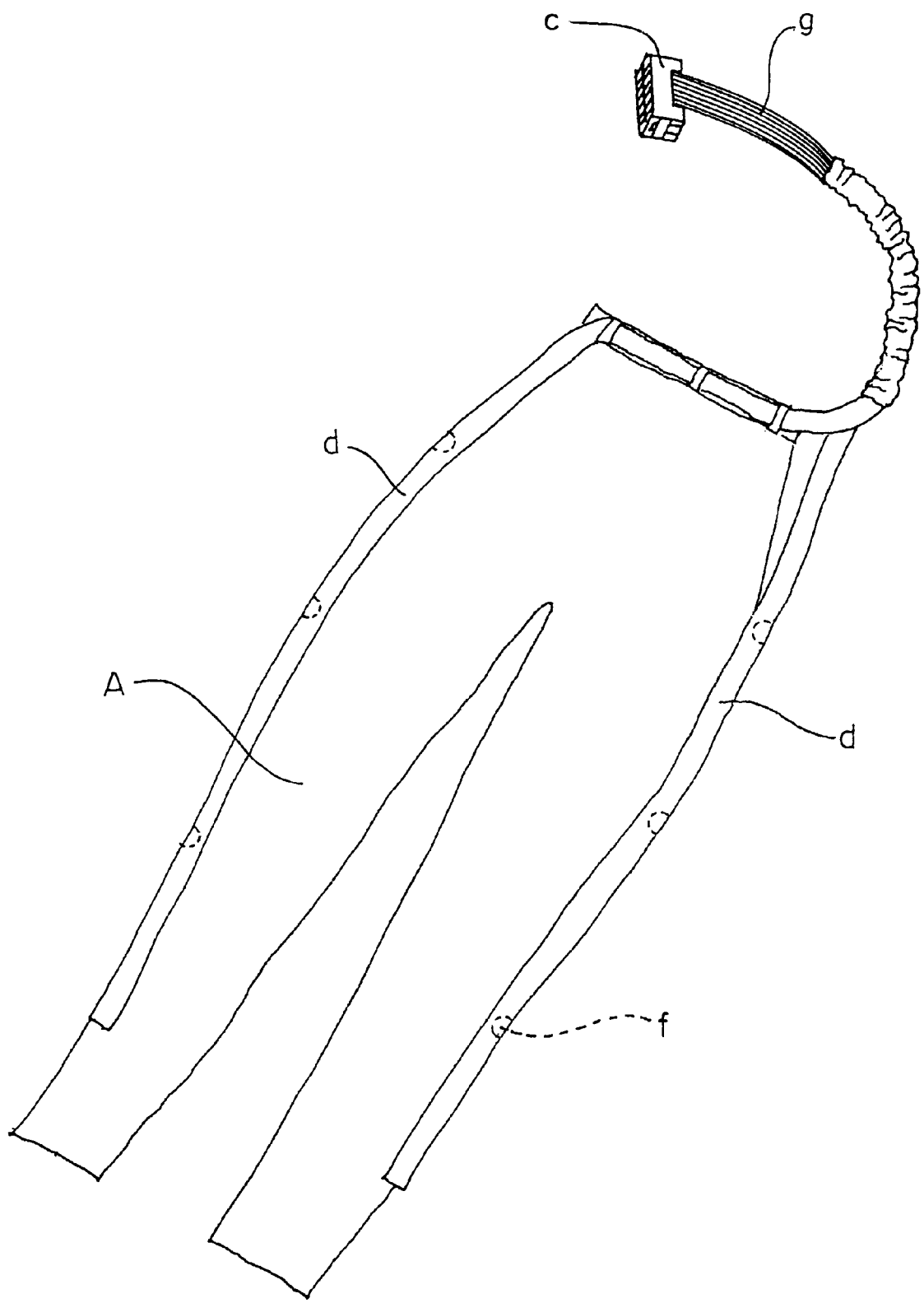
FIG. 10 illustrates two bundles of electric wires attached to the opposite outer sides and waist-surrounding part of the garment.

As shown in FIG. 10, the elongated tubular bag "d" is attached to either outer side of the pair of electroded tights "A" by making the relay terminals "f" to snap in the electrically conductive press studs The elongated tubular bag "d" is washable. It is unfastened to remove the bundle of electric wires "g" from the relay terminals "f", and then, the tubular bag "d" is removed from the pair of electroded tights "A" to be washed.

The tubular bag "d" is preferably made of the same stretch cloth as the pair of electroded tights because otherwise, a wearer may have insufficient stretch feeling locally.

Figure 11:
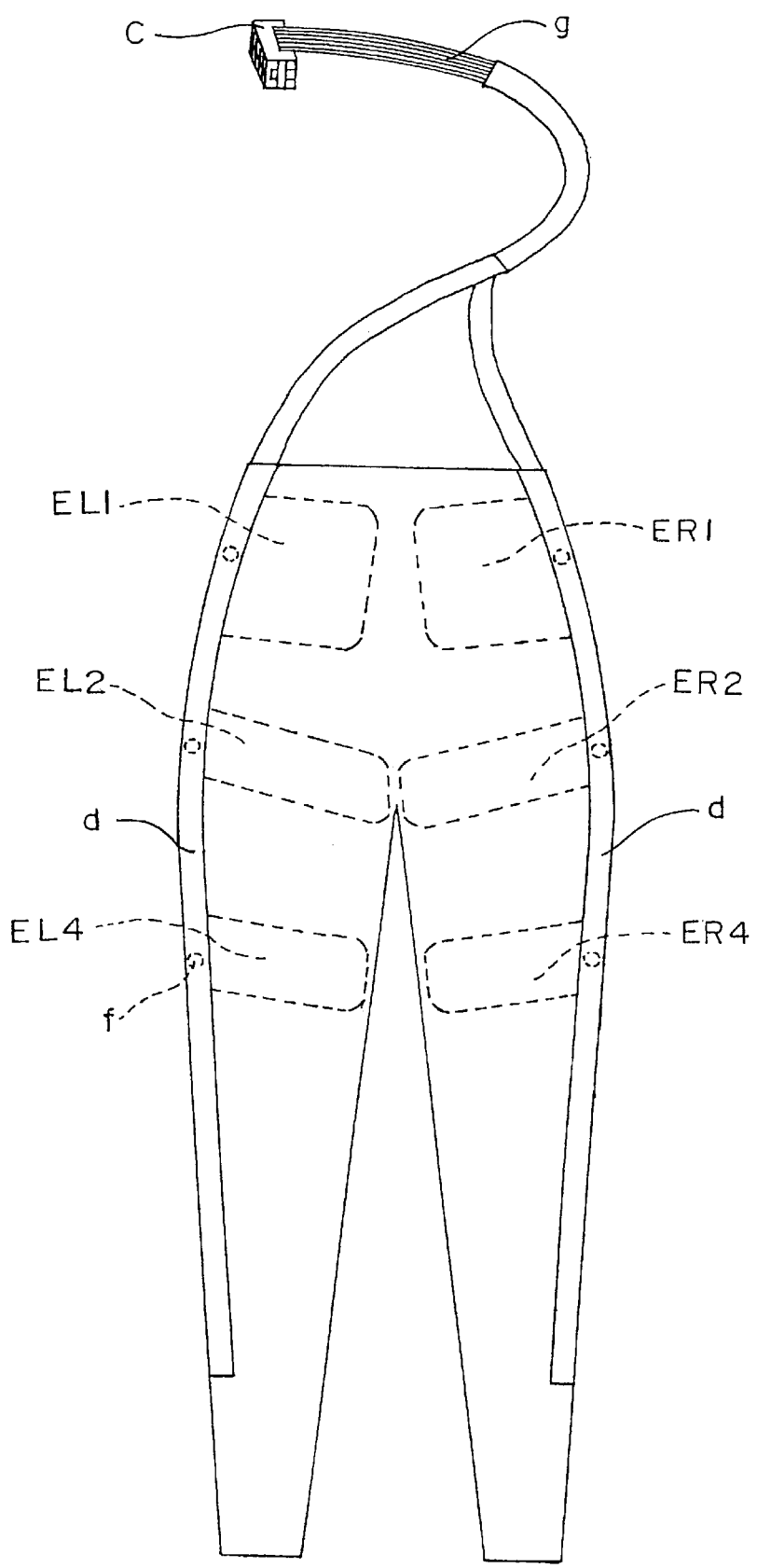
FIG. 11 is a front view of another pair of electroded tights.
Figure 12:
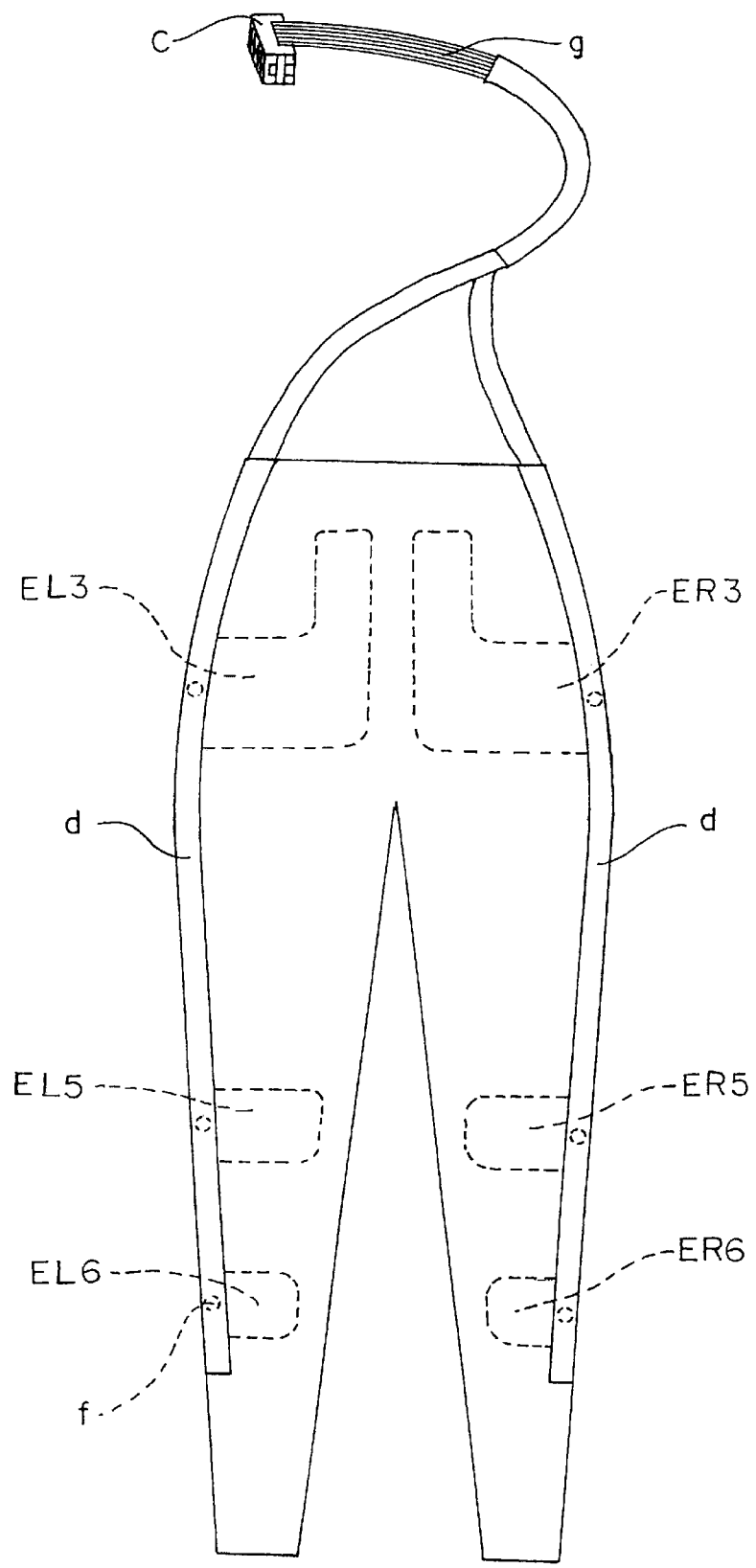
FIG. 12 is a rear view of the pair of electroded tights of FIG. 11.

FIGS. 11 and 12 illustrate the front and rear sides of a pair of tights A having two elongated tubular bags "d" attached to the opposite sides of the pair of tights A.

Figure 13:
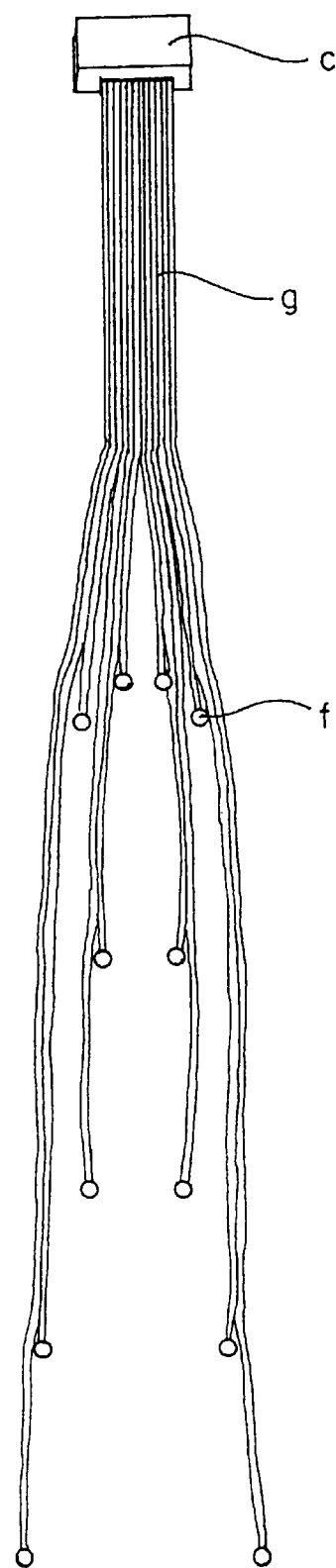
FIG. 13 a bundle of flat arrangement of electric wires.

FIG. 13 shows a bundle of flat arrangement of electric wires g similar to the bundle of electric wires "b" in structure.

The present invention permits one to take a beauty treatment by wearing a pair of electroded tights, which has a plurality of flat electrodes attached inside.

One can have, therefore, a beauty treatment without taking off one's cloth, thus facilitating the practice of beauty treatment even in presence of people.

The beauty treatment does not require that one is naked to lie down, permitting any way of holding one's body. Thus, one is permitted to stand, sit in a chair, walk, work or take an exercise.

Advantageously a pair of electroded tights can be so sized as to fit one's body with its flat electrodes applied exactly to selected treatment-effective points of the body.

The pair of tights is made of such a stretch material that the electrodes are pushed against the body. Also, the very close fitting garment covers the legs and lower part of the body tightly, and therefore, the tight fitting along with the expediting of blood circulation and lymph flow caused by the pulsating stimulation has the effect of preventing the appearance of dropsy, which would otherwise, appear on the legs while working on one's feet.

As described in claim 1, a bundle of electric wires to be connected to the flat electrodes can be contained in an elongated tubular bag, thereby preventing the tangling of electric wires which otherwise, would be caused, and at the same time, facilitating the attaching and removing of the electric wires from a pair of electroded tights while improving the appearance of the pair of electroded tights.

What is claimed is:

1. In a pulse beauty treatment apparatus, a pair of electrode tights made of a stretch material having a plurality of flat electrodes of soft inside, stretch material, which flat electrodes being adapted to be connected to an associated pulse generator, wherein said electrode tights comprise an elongated tubular bag for containing a bundle of electric wires, which are to be connected to said flat electrodes, said elongated tubular bag having a fastener running along its full length for holding together two parts of said bag, and a plurality of relay terminals fixed inside for connecting said electric wires to said flat electrodes.

* * * * *